US008986271B1

(12) United States Patent
Horne

(10) Patent No.: US 8,986,271 B1
(45) Date of Patent: Mar. 24, 2015

(54) URINE POUCH AND ASSOCIATED USE THEREOF

(71) Applicant: Jayne M. Horne, Alpine, CA (US)

(72) Inventor: Jayne M. Horne, Alpine, CA (US)

( * ) Notice: Subject to any disclaimer, the term of this patent is extended or adjusted under 35 U.S.C. 154(b) by 175 days.

(21) Appl. No.: 13/751,422

(22) Filed: Jan. 28, 2013

(51) Int. Cl.
*A61F 5/44* (2006.01)
*A61F 13/56* (2006.01)
*A61F 13/471* (2006.01)
*A61F 5/453* (2006.01)

(52) U.S. Cl.
CPC ............ *A61F 13/5611* (2013.01); *A61F 5/4408* (2013.01); *A61F 5/453* (2013.01); *A61F 13/471* (2013.01); *A61F 5/44* (2013.01)
USPC ........................ 604/349; 604/353; 604/385.09

(58) Field of Classification Search
CPC ......... A61F 5/44; A61F 5/4408; A61F 5/451; A61F 5/453; A61F 2005/4402; A61F 13/471; A61F 13/4915
USPC ........ 604/346, 347, 349–354, 385.09, 385.11
See application file for complete search history.

(56) References Cited

U.S. PATENT DOCUMENTS

| 4,387,726 | A | * | 6/1983 | Denard | ........................ 600/573 |
| 4,601,716 | A | | 7/1986 | Smith | |
| 5,275,592 | A | | 1/1994 | Grizzaffi | |
| 5,283,912 | A | * | 2/1994 | Chung | .............................. 2/403 |
| 5,383,867 | A | * | 1/1995 | Klinger | ..................... 604/385.23 |
| 5,649,913 | A | * | 7/1997 | Cohen | ........................... 604/353 |
| 5,807,299 | A | * | 9/1998 | McRoberts et al. | ............ 602/67 |
| 6,059,762 | A | * | 5/2000 | Boyer et al. | .................. 604/349 |
| 6,197,011 | B1 | * | 3/2001 | Freitas et al. | ............ 604/385.03 |
| 6,419,665 | B1 | * | 7/2002 | Cohen | ........................... 604/349 |
| 6,635,038 | B2 | * | 10/2003 | Scovel | ......................... 604/353 |
| 7,344,526 | B2 | * | 3/2008 | Yang et al. | .................... 604/393 |
| 8,425,482 | B2 | * | 4/2013 | Khoubnazar | ............ 604/385.09 |
| 2003/0028161 | A1 | * | 2/2003 | Carballo | ....................... 604/349 |
| 2004/0106909 | A1 | | 6/2004 | Browning | |
| 2013/0018350 | A1 | * | 1/2013 | McNulty | .................. 604/385.03 |

* cited by examiner

*Primary Examiner* — Lynne Anderson

(57) ABSTRACT

A urine pouch includes a sheath to be worn beneath the underclothes of males and to accommodate the penis. Such an arrangement may absorb and retain in a discreet and effective manner any accidental discharge of urine by the user. The apparatus may be worn beneath the underwear of the user and held in place by a flap which extends upwardly above the genital region and folds over the waistband of the wearer's briefs or boxers. The apparatus may further extend downwardly such that the penis may be inserted through a serrated opening and thereby pushed or pulled through to hold the penis in place. The cross-shaped opening may further be easy to tear to accommodate the entry of the penis into the sheath. The apparatus may further include a waistband for securing to the wearer's undergarment.

11 Claims, 3 Drawing Sheets

URINE POUCH AND ASSOCIATED USE THEREOF

CROSS REFERENCE TO RELATED APPLICATIONS

Figure 1:
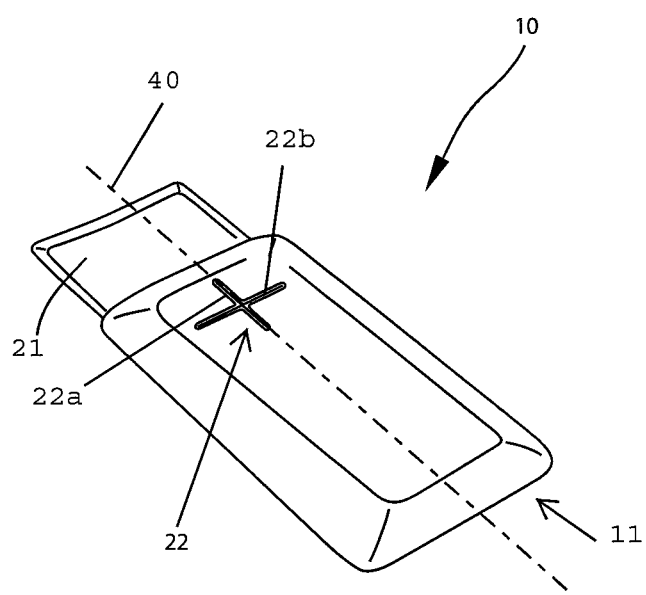

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF NON-LIMITING EXEMPLARY EMBODIMENT(S) OF THE PRESENT DISCLOSURE

TECHNICAL FIELD

This non-limiting exemplary embodiment(s) relates to urinary incontinence garments and, more particularly, to a urine pouch for providing users with an easy and convenient means of absorbing and retaining urinary fluid discharge from a male penis that is caused by urinary incontinence.

PRIOR ART

Some inventions such as cars, light bulbs, television, personal computers, and cell phones change the way we live and change the world. These are what one might call groundbreakers: entirely new technologies or adaptations of existing technology to accomplish things not previously thought possible. Such inventions mark the great milestones in humanity's technological history, and bring on huge changes in the life of a society. But groundbreaking inventions are understandably rare: the great majority of successful inventions are instead small improvements that come into play gradually, so subtly that we hardly notice them.

Improvement-type inventions bring not sweeping societal change, but heightened individual convenience that then spreads to all consumers or subtle, hardly noticed improvements in specific, pre-existing technologies. Does anyone remember the date when the first spray-pump bottle hit the shelves? How about the first camera with a built-in flash, or the first time they saw VELCRO®? Who remembers the arrival of the electric toothbrush, disposable flossers, or soft-drink bottles made of plastic? Who can name the person who invented the automobile shoulder-harness, anti-lock brakes, or disposable razors? Inventions such as these often, simple improvements of existing products make our lives easier (whether we notice them or not), and very soon we cannot remember a time without them.

In regard to almost anything, then, avenues to further improvement are open to the inventor's creative vision. Often, improvement inventions are the inspiration of persons who work daily in a specialized field or trade, and create out of necessity, frustration and imagination a new and better tool or method for improving their working life and that of their co-workers: or, as in the invention to be unveiled, described, and discussed in the course of this report, their patients. In this aspect, in caring for elderly male patients, many of whom suffer from urinary incontinence, two essential facts are perceived. First, the adult incontinence products currently on the market are designed primarily with women in mind, and are generally more along the line of an adult diaper than what a man with urinary incontinence would need; and second, it is noted that urinary incontinence can be a problem for a male of any age, from a toddler to a teen to a senior citizen.

Accordingly, a need remains for a urine collection apparatus in order to overcome prior art shortcomings. The exemplary embodiment(s) satisfy such a need by providing a urine pouch that is convenient and easy to use, lightweight yet durable in design, versatile in its applications, and designed for absorbing and retaining urinary fluid that is discharged from a male penis, as a result of urinary incontinence.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a urine pouch for providing users with an easy and convenient means of absorbing and retaining urinary fluid discharge from a male penis that is caused by urinary incontinence. These and other objects, features, and advantages of the non-limiting exemplary embodiment(s) are provided by a urine pouch adapted for absorbing and retaining urinary fluid discharge caused by urinary incontinence. Such a urine pouch includes a flexible sheath having lines of weakness formed therein, a flexible flap attached to the sheath, and a flexible waistband attached to the flap. Advantageously, the waistband has an adhesive layer capable of being removably secured to a user undergarment such that the lines of weakness are severed by pinching the sheath and tugging downwardly away from the waistband while the flap remains attached to the waistband.

In a non-limiting exemplary embodiment, the sheath is formed from fluid impermeable material including a front wall and a rear wall attached thereto. A closed bottom end is formed at respective bottom edges of the front and rear walls, and a top opening is formed at respective top edges of the front and rear walls. Advantageously, the flap is integrally coupled to the rear wall and spaced from the front wall such that the flap remains anterior of the top opening.

In a non-limiting exemplary embodiment, the lines of weakness include a first linear line of weakness registered parallel to a longitudinal axis of the sheath, and a second linear line of weakness registered orthogonal to the longitudinal axis of the sheath. Advantageously, the first and second lines of weakness intersect and are configured in a crisscross pattern.

In a non-limiting exemplary embodiment, the lines of weakness are located proximate to the top opening and distal to the closed bottom end such that the lines of weakness are capable of receiving a penis therethrough.

In a non-limiting exemplary embodiment, each of the first and second lines of weakness are formed at the front wall and spaced from the rear wall.

In a non-limiting exemplary embodiment, the waistband includes inner and outer circumferential faces extending along an entire circumference of the waistband. The flap is connected to the outer circumferential face of the waistband such that the top opening and the lines of weakness are freely pivotally towards and away from the inner circumferential face of the waistband.

In a non-limiting exemplary embodiment, the flap is slidably coupled to the waistband and thereby adjustably displaced along the outer circumferential face of the waistband.

The present disclosure further includes a method of utilizing a urine pouch for absorbing and retaining urinary fluid discharge caused by urinary incontinence. Such a method includes the chronological steps of: providing a flexible sheath having lines of weakness formed therein; providing and attaching a flexible flap to the sheath; providing and attaching a flexible waistband to the flap; removably securing an adhesive layer of the waistband to a user undergarment; and severing the lines of weakness by pinching the sheath and tugging downwardly away from the waistband while the flap remains attached to the waistband.

There has thus been outlined, rather broadly, the more important features of non-limiting exemplary embodiment(s) of the present disclosure so that the following detailed description may be better understood, and that the present contribution to the relevant art(s) may be better appreciated. There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

Figure 2:
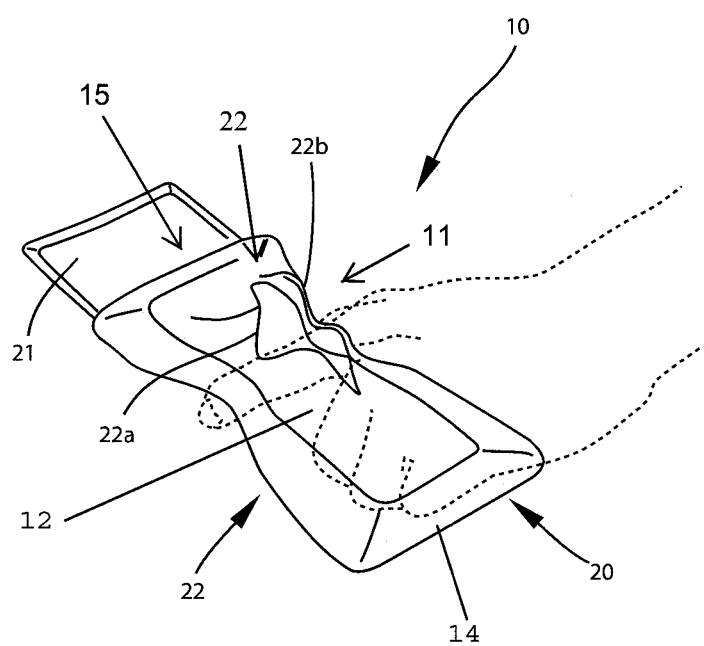
Figure 3:
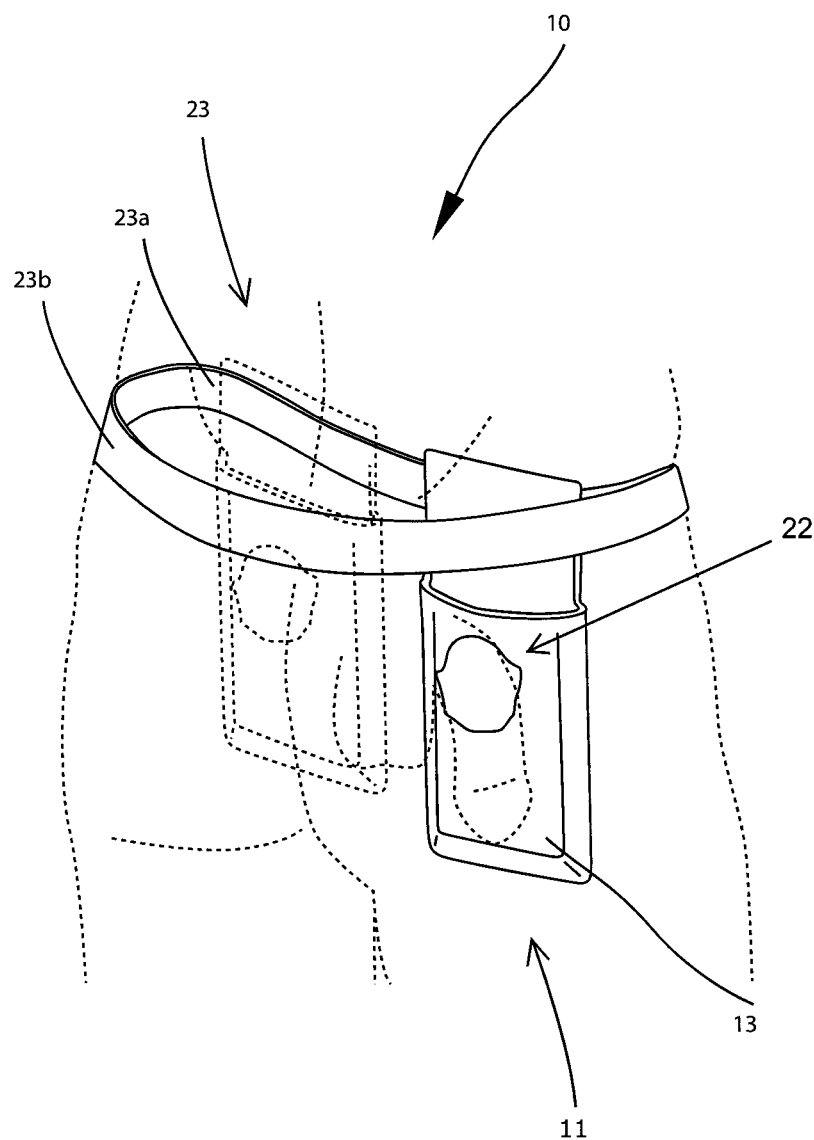

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

FIG. 1 is a perspective view showing a sheath of a urine pouch for providing users with an easy and convenient means of absorbing and retaining urinary fluid discharge from a male penis that is caused by urinary incontinence, in accordance with the non-limiting exemplary embodiment(s);

FIG. 2 is a perspective view of the sheath shown in FIG. 1 wherein the lines of weakness are separate by squeezing the pouch; and FIG. 3 is a perspective rear elevational view showing the sheath slidably attached to a waistband wherein the waistband has an adhesive layer capable of being removably secured to a user undergarment such that the lines of weakness are severed by pinching the sheath and tugging downwardly away from the waistband while the flap remains attached to the waistband.

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s). Like numbers refer to like elements throughout the figures.

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

The non-limiting exemplary embodiment(s) is/are referred to generally in FIGS. 1-3 and is/are intended to provide a urine pouch 10 for providing users with an easy and convenient means of absorbing and retaining urinary fluid discharge from a male penis that is caused by urinary incontinence. It should be understood that such non-limiting exemplary embodiment(s) may be used to absorbing various types of bodily fluids, and should not be limited to the uses described herein.

Referring to the figures in general, in a non-limiting exemplary embodiment, a urine pouch 10 adapted for absorbing and retaining urinary fluid discharge caused by urinary incontinence. Such a urine pouch 10 includes a flexible sheath 11 having lines of weakness 22 formed therein, a flexible flap 21 attached to the sheath 11, and a flexible waistband 23 attached to the flap 21. Advantageously, the waistband 23 has an adhesive layer capable of being removably secured to a user undergarment such that the lines of weakness 22 are severed by pinching the sheath 11 and tugging downwardly away from the waistband 23 while the flap 21 remains attached to the waistband 23.

In a non-limiting exemplary embodiment, the sheath 11 is formed from fluid impermeable and/or fluid absorbing material including a front wall 12 and a rear wall 13 attached thereto. A closed bottom end 14 is formed at respective bottom edges of the front and rear walls 13, 14, and a top opening 15 is formed at respective top edges of the front and rear walls 13, 14. Advantageously, the flap 21 is integrally coupled to the rear wall 13 and spaced from the front wall 12 such that the flap 21 remains anterior of the top opening 15 and does not interfere with adjustable positioning of the penis.

In a non-limiting exemplary embodiment, the lines of weakness 22 include a first linear line of weakness 22a registered parallel to a longitudinal axis 40 of the sheath 11, and a second linear line of weakness 22b registered orthogonal to the longitudinal axis 40 of the sheath 11. Advantageously, the first and second lines of weakness 22a, 22b intersect and are configured in a crisscross pattern.

In a non-limiting exemplary embodiment, the lines of weakness 22 are located proximate to the top opening 15 and distal to the closed bottom end 14 such that the lines of weakness 22 are capable of receiving a penis therethrough.

In a non-limiting exemplary embodiment, each of the first and second linear lines of weakness 22a, 22b are formed at the front wall 12 and spaced from the rear wall 13.

In a non-limiting exemplary embodiment, the waistband 23 includes inner and outer circumferential faces 23a, 23b extending along an entire circumference of the waistband 23. The flap 21 is connected to the outer circumferential face 23b of the waistband 23 such that the top opening 15 and the lines of weakness 22 are freely pivotal towards and away from the inner circumferential face 23a of the waistband 23.

In a non-limiting exemplary embodiment, the flap 21 is slidably coupled to the waistband 23 and thereby adjustably displaced along the outer circumferential face 23b of the waistband 23 such that the sheath 11 does not shift away from the penis when a user twists and turns while walking, jump, running, sleeping, etc.

In a non-limiting exemplary embodiment, the urine pouch 10 preferably includes a highly absorbent, sanitary-lined sack, or loose-fitting sheath 11 designed to be worn beneath the underclothes of males and to accommodate the penis and sized for males ranging from toddlers to adults to the elderly. Such an arrangement may absorb and retain in a discreet and effective manner any accidental discharge of urine by the user. A water-impermeable layer may be wrapped about the water-absorbent layer. The pouch 10 may be worn beneath the underwear of the user and held in place by a flap 21 which extends upwardly above the genital region and adhesively folds over (e.g., attaches) the waistband 23 of the wearer's briefs or boxers. The pouch 10 may further extend downwardly such that the penis may be inserted through a crisscrossed opening 22 (lines of weakness) and thereby pushed or pulled through to hold the penis in place.

In a non-limiting exemplary embodiment, the dimensions of the pouch 10 may vary according to the age and size of the individual. As a non-limiting example, the sheath 11 for youngsters may measure 5" in total length by 3" in width, and may be sold in 12-unit packs; for teens. The sheath 11 for teens may measure 7" in total length by 4" in width, and be sold in 24-unit packs. For adult men, the sheath 11 may measure 9" in total length and 5" in width, and be sold in 36 or 48-unit packs. The cross-shaped opening 22 may further be easy to tear to accommodate the entry of the penis into the sheath 11 of the pouch 10. Men of larger-than-average size may simply insert their penis into the pocket portion of the pouch 10, leaving the scored opening 22 intact. The pouch 10 may further include a waistband 23 for securing to the wearer's boxers or briefs.

The present disclosure further includes a method of utilizing a urine pouch 10 for absorbing and retaining urinary fluid discharge caused by urinary incontinence. Such a method includes the chronological steps of: providing a flexible sheath 11 having lines of weakness 22 formed therein; providing and attaching a flexible flap 21 to the sheath 11; providing and attaching a flexible waistband 23 to the flap 21; removably securing an adhesive layer of the waistband 23 to a user undergarment; and severing the lines of weakness 22 by pinching the sheath 11 and tugging downwardly away from the waistband 23 while the flap 21 remains attached to the waistband 23.

There are several significant benefits and advantages associated with the urine pouch 10. As a non-limiting example, the urine pouch 10 provides a highly absorbent, discreet, and disposable urinary-incontinence protection for males of all ages. Equally suitable for a toddler or little boy done with potty training but still having difficulty controlling his bladder, an elderly man in a nursing or assisted-living facility, a man afflicted by the urinary problems that prostate problems entail, a youth who has become paraplegic due to an accident, wound, or injury, The pouch 10 may free a boy or man from the need to wear bulky and cumbersome incontinence briefs, yet provide him reliable, effective protection, dryness, and confidence.

In use, the urine pouch 10 would be simple and straightforward to use. First, the user may wear the pouch 10 beneath his underwear and insert his penis through the easy to tear crisscrossed opening 22 and thereby pushed or pulled through to hold his penis in place. For men of larger-than-average size, they may simply insert their penis into the pocket portion 15 of the sheath 11, leaving the scored opening 22 (lines of weakness) intact. The pouch 10 may simply be discarded when filled with urine after use and be replaced with a new one.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. §1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A urine pouch adapted for absorbing and retaining urinary fluid discharge caused by urinary incontinence, said urine pouch comprising:
   a sheath having lines of weakness formed therein;
   a flap attached to said sheath; and
   a waistband attached to said flap;
   wherein said waistband has an adhesive layer capable of being removably secured to a user undergarment such that said lines of weakness are severed by pinching said sheath and tugging downwardly away from said waistband while said flap remains attached to said waistband;
   wherein said waistband comprises: inner and outer circumferential faces extending along an entire circumference of said waistband, said flap being connected to said outer circumferential face of said waistband such that said top opening and said lines of weakness are freely pivotally towards and away from said inner circumferential face of said waistband;
   wherein said flap is slidably coupled to said waistband and thereby adjustably displaced along said outer circumferential face of said waistband.

2. The urine pouch of claim 1, wherein said sheath is formed from fluid impermeable material comprising:
   a front wall and a rear wall attached thereto;
   a closed bottom end formed at respective bottom edges of said front and rear walls; and
   a top opening formed at respective top edges of said front and rear walls;
   wherein said flap is integrally coupled to said rear wall and spaced from said front wall such that said flap remains anterior of said top opening.

3. The urine pouch of claim 2, wherein said lines of weakness comprise:
   a first linear line of weakness registered parallel to a longitudinal axis of said sheath;
   a second linear line of weakness registered orthogonal to the longitudinal axis of said sheath;
   wherein said first and second linear lines of weakness intersect and are configured in a crisscross pattern.

4. The urine pouch of claim 3, wherein said lines of weakness are located proximate to said top opening and distal to said closed bottom end such that said lines of weakness are capable of receiving a penis therethrough.

5. The urine pouch of claim 4, wherein each of said first and second linear lines of weakness are formed at said front wall and spaced from said rear wall.

6. A urine pouch adapted for absorbing and retaining urinary fluid discharge caused by urinary incontinence, said urine pouch comprising:
   a flexible sheath having lines of weakness formed therein;
   a flexible flap attached to said sheath; and
   a flexible waistband attached to said flap;
   wherein said waistband has an adhesive layer capable of being removably secured to a user undergarment such that said lines of weakness are severed by pinching said sheath and tugging downwardly away from said waistband while said flap remains attached to said waistband;
   wherein said sheath is formed from fluid impermeable material comprising:
   a front wall and a rear wall attached thereto;
   a closed bottom end formed at respective bottom edges of said front and rear walls; and
   a top opening formed at respective top edges of said front and rear walls;
   wherein said flap is integrally coupled to said rear wall and spaced from said front wall such that said flap remains anterior of said top opening.

7. The urine pouch of claim 6, wherein said lines of weakness comprise:
   a first linear line of weakness registered parallel to a longitudinal axis of said sheath;
   a second linear line of weakness registered orthogonal to the longitudinal axis of said sheath;
   wherein said first and second linear lines of weakness intersect and are configured in a crisscross pattern.

8. The urine pouch of claim 7, wherein said lines of weakness are located proximate to said top opening and distal to said closed bottom end such that said linear lines of weakness are capable of receiving a penis therethrough.

9. The urine pouch of claim 8, wherein each of said first and second linear lines of weakness are formed at said front wall and spaced from said rear wall.

10. The urine pouch of claim 6, wherein said waistband comprises: inner and outer circumferential faces extending along an entire circumference of said waistband, said flap being connected to said outer circumferential face of said waistband such that said top opening and said lines of weakness are freely pivotally towards and away from said inner circumferential face of said waistband.

11. The urine pouch of claim 10, wherein said flap is slidably coupled to said waistband and thereby adjustably displaced along said outer circumferential face of said waistband.

* * * * *